United States Patent
Danielsen et al.

(10) Patent No.: US 10,246,739 B2
(45) Date of Patent: Apr. 2, 2019

(54) EXONUCLEASE CYCLING ASSAY

(71) Applicant: GEORGETOWN UNIVERSITY, Washington, DC (US)

(72) Inventors: Mark Danielsen, Germantown, MD (US); Berenice Alfonso, Fairfax, VA (US); Bolor Tumurpurev, Washington, DC (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 14/212,151

(22) Filed: Mar. 14, 2014

(65) Prior Publication Data

US 2014/0349286 A1    Nov. 27, 2014

Related U.S. Application Data

(60) Provisional application No. 61/962,300, filed on Mar. 15, 2013.

(51) Int. Cl.
*C12Q 1/68* (2018.01)
*C12Q 1/6823* (2018.01)

(52) U.S. Cl.
CPC .................. *C12Q 1/6823* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS

| 5,716,784 A | 2/1998 | Di Cesare |
| 2008/0213762 A1* | 9/2008 | Yamamoto ............ C12Q 1/6827 435/6.12 |

OTHER PUBLICATIONS

Lambda Exonuclease from NEB. Printed on Jan. 19, 2016.*
Properties of Exonucleases and Endonucleases from NEB. Printing on Sep. 22, 2016.*
Copley and Boot, Biotechniques, 13(6):888-92 (1992).
Little, Journal of Biological Chemistry, 242(4): 679-86 (1967).
Okano and Kambara, Analytical Biochem, 288:101-8 (1995).

* cited by examiner

*Primary Examiner* — Frank W Lu
(74) *Attorney, Agent, or Firm* — Ratnerprestia

(57) ABSTRACT

The present invention relates to a novel method for detecting a target polynucleotide having a target sequence, comprising hybridizing the target polynucleotide with a probe to form a hybrid; exposing the hybrid to a 5' exonuclease so that the probe in the hybrid is digested and the target polynucleotide is dissociated from the digested probe; repeating the hybridization step and the digestion step; and detecting the digested probes. The presence of the digested probes indicates the presence of the target polynucleotide.

17 Claims, 2 Drawing Sheets

Specification includes a Sequence Listing.

```
SEQUENCE LISTING

<160> NUMBER OF SEQ ID NOS: 2

<210> SEQ ID NO 1
<211> LENGTH: 17
<212> TYPE: DNA
<213> ORGANISM: Bacillus anthracis

<400> SEQUENCE: 1
aggatcttac gaaactt                                                      17

<210> SEQ ID NO 2
<211> LENGTH: 20
<212> TYPE: DNA
<213> ORGANISM: Bacillus anthracis

<400> SEQUENCE: 2
ccgaagtttc gtaagatcct                                                   20
```

EXONUCLEASE CYCLING ASSAY

CROSS-REFERENCE TO RELATED APPLICATION

This application claims the benefit of U.S. Provisional Application No. 61/962,300, filed Mar. 15, 2013, the contents of which are incorporated herein by reference in their entireties for all purposes.

FIELD OF THE INVENTION

The invention relates generally to methods for the detection of specific nucleotide sequences using exonuclease cycling assays, and reagents and kits for use in practicing the methods.

BACKGROUND OF THE INVENTION

It is often desirable to detect specific DNA sequences in a mixture of sequences or in a sample that contains DNA and other ingredients. For instance, detection of specific DNA sequences is often used to determine whether a particular bacterium is present in a biological sample. Many techniques can be used including cycling assays such as polymerase chain reaction (PCR) and exonuclease cycling assays, in which exonucleases are used to digest probes. Lambda exonuclease has been used in an exonuclease cycling assay to digest double stranded DNA (dsDNA) from its 5' end (Copley and Boot, Exonuclease Cycling Assay: An Amplified Assay for the Detection of Specific DNA Sequences, *Biotechniques* 1992 December; 13(6):888-92). Lambda exonuclease has very little activity on a single stranded DNA (ssDNA). Digestion by lambda exonuclease requires a phosphate at the 5' end of the DNA strand to be digested. The 5' exonuclease activity of a DNA polymerase (Taq polymerase) is used for real time PCR analysis. This assay requires both DNA synthesis and probe digestion by the exonuclease activity of the polymerase (U.S. Pat. No. 5,716,784). It also requires a probe with a blocked 3' end. The 3' exonuclease activity of exonuclease III has been used for a cycling reaction (Okano and Kambara, DNA Probe Assay Based on Exonuclease III Digestion of Probes Hybridized on Target DNA, *Analytical Biochem* 1995; 288, 101-8), but the background is extremely high.

The exonuclease cycling assay has a number of drawbacks. First, the assay tends to have high background activity. Second, both probe and target DNA can be degraded preventing a cycling assay where a probe binds and is degraded in a cycling reaction. Third, the enzyme requires a 5' phosphate. This limits the position and type of modifications that can be made to the probe. Thus, there remains a need for a reliable and sensitive exonuclease cycling assay to detect specific nucleotide sequences.

SUMMARY OF THE INVENTION

The present invention relates to methods for detecting a polynucleotide having a unique sequence and related reagents and kits.

According to one aspect of the present invention, a method for detecting a target polynucleotide is provided. The target polynucleotide comprises a target sequence. The method comprises (a) hybridizing the target polynucleotide with a probe having a sequence complementary with the target sequence and lacking a phosphorylated 5' end, whereby a hybrid of the probe and the target polynucleotide is formed, wherein the hybrid comprises a hybridization region formed between the target sequence and the probe; (b) exposing the hybrid to a 5' exonuclease, whereby the probe in the hybrid is digested and the target polynucleotide is dissociated from the digested probe; (c) repeating steps (a) and (b); and (d) detecting the digested probes. The presence of the digested probes indicates the presence of the target polynucleotide.

The 5' exonuclease may be lambda exonuclease or T7 exonuclease, preferably lambda exonuclease. The probe may have a quencher at its 5' end and a fluor internally or at the 3' end.

The target polynucleotide may be a DNA or RNA, preferably a DNA. The target polynucleotide may be protected against digestion by the 5' exonuclease. The target polynucleotide may have one or more nuclease resistant nucleotides upstream of the hybridization region. The target polynucleotide may have one or more uncleavable linkages upstream of the hybridization region. The target polynucleotide may be prepared by polymerase synthesis using a 5' exonuclease protected primer. The 5' exonuclease protected primer may lack a 5' phosphate group. The 5' exonuclease protected primer may contain one or more uncleavable nucleotide linkages. The 5' exonuclease protected primer may be chemically modified. The polymerase synthesis may be selected from the group consisting of multiple displacement amplification (MDA), polymerase chain reaction (PCR), rolling circle amplification, nondisplacement amplification and reverse transcription. The target DNA polynucleotide may be synthesized from one or more short polynucleotides, wherein the one or more short oligonucleotides are resistant to digestion by the 5' exonuclease.

The method according to the present invention may further comprise determining the amount of the digested probes. The amount of the digested probes indicates the rate of the detection method.

The target polynucleotide may be detected in a homogenous mixture. The detection limit may be 1 pmole, 100 fmole or 10 fmole. Preferably, the detection limit is 10 fmole.

According to another aspect of the present invention, a kit is provided for each detection method of the present invention. The kit comprises a probe and a 5' exonuclease.

DETAILED DESCRIPTION OF THE INVENTION

Figure 1:
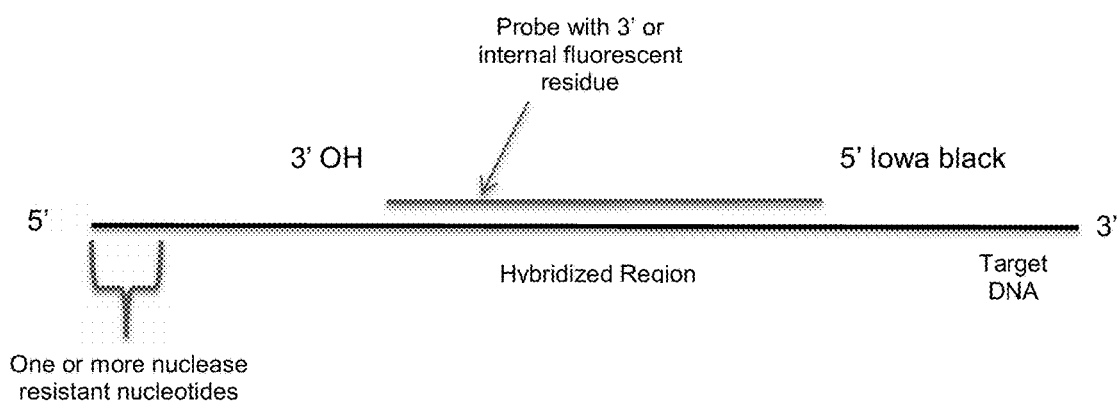
FIG. 1 is a diagram illustrating an exemplary detection assay according to some embodiments of the disclosed subject matter.
Figure 2:
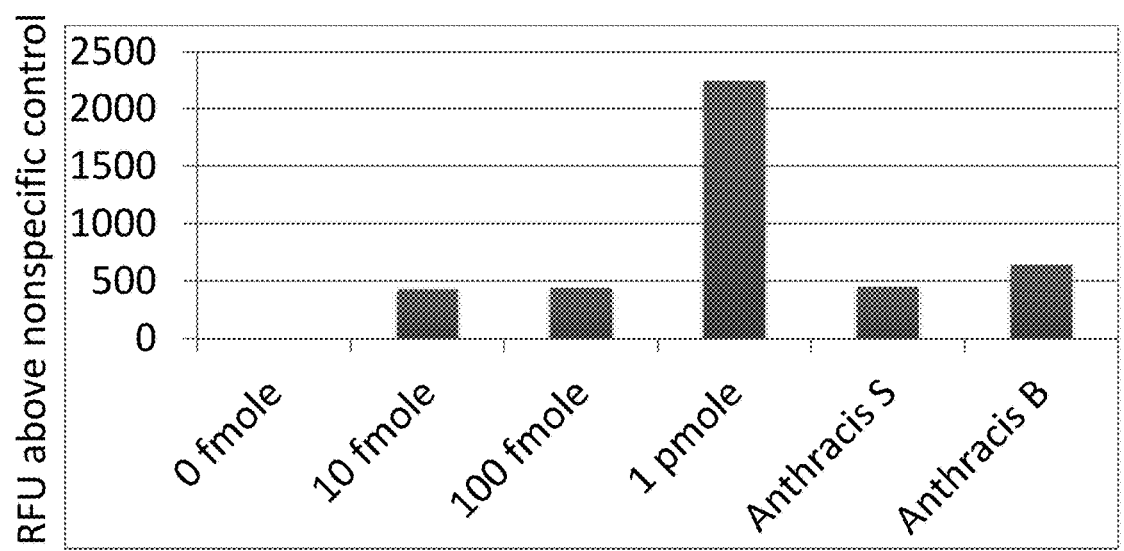
FIG. 2 shows the results of an exonuclease cycling assay reaction.

The present invention relates to a novel sensitive method for detecting a specific nucleotide sequence in a target polynucleotide using an exonuclease cycling assay. It has been discovered that modification of the 5' end of oligonucleotides with fluorescein results in oligonucleotides resistant to the exonuclease activity of lambda exonuclease. Unexpectedly, the quencher Iowa Black FQ at the 5' position allows degradation of double stranded DNA by lambda exonuclease.

The present invention provides a system having low (near undetectable) levels of background activity in the absence of a target polynucleotide but has high activity in its presence.

This system may use an oligonucleotide probe that has a fluor anywhere except at the 5' end and a quencher located at the 5' end. Accordingly, the oligonucleotide probe is not phosphorylated as the quencher acts as a 5' phosphate replacement.

The term "complementary" as used herein refers to the ability of two nucleotide strands, either two DNA strands or a DNA strand and a RNA strand, to form a double stranded duplex having, for example, at least about 80%, 90%, 95%, or 99%, preferably at least about 90%, more preferably at least 95%, most preferably completely 100%, matching purine bases and pyrimidine bases, Two complementary nucleotide strands may have fewer than about 5, 4, 3, 2 or 1 base mismatches.

The term "hybridization" or "hybridizing" as used herein refers to joining two complementary nucleotide strands to form a hybrid, i.e., a duplex of DNA/DNA or DNA/RNA. The two nucleotide strands may be complementary with each other perfectly, i.e., having 100% matching bases, or partially, i.e., having less than 100% matching bases. Hybridization conditions can be chosen by a skilled practitioner to provide a desired degree of sequence specific hybridization. In various embodiments, one or more base mismatches may be permitted, or perfect complementarity may be required.

The term "5' exonuclease" as used herein refers to an enzyme that cleaves nucleotides progressively from the 5' end of a nucleotide strand and is in a hybrid, or a duplex of DNA/DNA or DNA/RNA. Preferably, the '5 exonuclease is capable of digesting nucleotides from a nucleotide strand having a 5' quencher. For example, the 5' exonuclease may be lambda exonuclease or Ti exonuclease. Preferably, the 5' exonuclease is lambda exonuclease.

The term "protected against" or "resistant" as used herein refers that less than about 80%, 50% or 20%, of a nucleotide strand (e.g., a target polynucleotide) is digested by a 5' exonuclease when exposed to the 5' exonuclease.

The term "target polynucleotide" used herein refers to any type of single stranded DNA or RNA. Preferably, the target polynucleotide is a single stranded DNA. A double stranded DNA may be converted into a single stranded DNA for use in the detection method according to the present invention. The target polynucleotide may be of any length. For example, the target polynucleotide may have at least about 25, 50, 100, 200 or 500 nucleotides. The target polynucleotide may be genomic DNA or RNA; denatured DNA or RNA; synthesized DNA or RNA; or DNA or RNA that has been purified. The target polynucleotide may be part of a heterogeneous sample, e.g., a biological or environmental sample. A biological sample is a sample obtained from a biological source, for example, serum, ascites fluid, cerebrospinal fluid, amniotic fluid, synovial fluid, pleural fluid, saliva, sputum, stool, urine, semen, tissue, biopsies, swabs, and the like from human and non-human sources. An environmental sample is a sample obtained from an environmental source such as air (aerosol sampling) water, soil and the like.

The target polypeptide comprises a target sequence. The target sequence may have about 5-50, preferably about 5-20, more preferably about 5-10 nucleotides, and may be identified uniquely.

The present invention provides a method for detecting a target polynucleotide having a target sequence. The method comprises (a) hybridizing the target polynucleotide with a probe so that a hybrid of the probe and the target polynucleotide is formed. The probe is a DNA oligonucleotide that has a sequence complementary with the target sequence and lacks a phosphorylated 5' end. The hybrid comprises a hybridization region formed between the target sequence and the probe. The method further comprises (b) exposing the hybrid to a 5' exonuclease so that the probe in the hybrid is digested and the target polynucleotide is dissociated from the digested probe. Once the target polynucleotide is release from the hybrid, one cycle is completed. The hybridizing step (a) and the digestion step (b) are then repeated in the next cycle. The dissociated target polynucleotide is hybridized with a new probe having a sequence complementary with the target sequence and lacking a phosphorylated 5' end. A newly formed hybrid of the target polynucleotide and the new probe is exposed to the 5' exonuclease. Upon exposure, the new probe in the hybrid is digested, and the target polynucleotide dissociates from the digested probe and is released from the hybrid. After repeating the hybridization step and the digestion step in multiple cycles, the digested probes are detected. The presence of the digested probes indicates the presence of the target polynucleotide.

In step (a), the target polynucleotide and the probe are maintained under conditions permitting the formation of a hybrid, i.e., double stranded nucleotides, comprising the target polynucleotide and the probe. Preferably, the target polynucleotide is a DNA and the hybrid is a double stranded DNA (dsDNA). The probe may have sufficient length and sequence similarity to allow hybridization of the probe with the target polynucleotide.

In step (b), the hybrid and the 5' exonuclease are maintained under conditions permitting cleavage or digestion of the probe in the hybrid and dissociation of the target polynucleotide from the cleaved or digested probe. As a result, the target polynucleotide is released from the hybrid, and remains to have the target sequence.

The target polypeptide may be protected against digestion by the 5' exonuclease using techniques known in the art. For example, the target polypeptide may have one or more nuclease resistant nucleotides (e.g., ribonucleotids) or uncleavable linkages (e.g., a C6 linker) upstream of the hybridization region, or may have a 5' hydroxyl.

The target polynucleotide protected from 5' exonuclease digestion may be prepared by polymerase synthesis using 5' exonuclease protected primers. The 5' exonuclease protected primer may lack a 5' phosphate group, have one or more uncleavable nucleotide linkages, or may be chemically modified. Examples of the polymerase synthesis include multiple displacement amplification (MDA), polymerase chain reaction (PCR), rolling circle amplification, nondisplacement amplification and reverse transcription. For example, PCR may be used to synthesize a target DNA while a reverse transcription may be used to synthesize a target RNA. Alternatively, the target polynucleotide may be synthesized from one or more short polynucleotides, which are resistant to digestion by the 5' exonuclease.

In one embodiment illustrated in FIG. 1, the target polynucleotide is a DNA. The target DNA is exposed to a probe having a 5' Iowa Black quencher, a 3' OH group, and a fluorescent residue internally. Upon hybridization of the probe with the target DNA, a hybrid of the probe and the target DNA is formed. The hybrid has a hybridization region formed by the probe and a sequence in the target DNA that is complementary with the probe sequence. The target DNA has one or more nuclease resistant nucleotides upstream of the hybridization region. For example, a target DNA having a 5' hydroxyl group making it resistant to lambda exonuclease activity.

The cleaved or digested probe may be detected based on the presence of a shortened DNA probe or the cleavage of a fluorescently labeled probe using techniques known in the art, including poly-acrylamide gel electrophoresis (PAGE), capillary electrophoresis (CE), and fluorescence resonance energy transfer (FRET). While CE is the most sensitive, FRET analysis may be performed in a real-time detection assay. For example, the probe may have a quencher (e.g., Iowa black) at the 5' end, as a replacement of the 5' phosphate group, and a fluor internally or at the 3' end. (FIG. 1). Two fluorescent labels may be used to increase the signal strength, or probes with different spectral characteristics may be used in multiplexing.

There are other ways to detect probe fragments. Optical detection methods may be used including bioluminescence and phosphorescence techniques, with or without resonance transfer (e.g., BRET and PRET). In addition, lanthanide-based energy transfer (LRET) may be used to observe the separation between appropriate labels. Mass Spectroscopy may be used with or without mass spectroscopy tags. Raman Spectroscopy is another option. Indeed, labeling of the probe with a surface enhanced Raman sphere can increase sensitivity many fold. Another way to detect the fragments produced relates to the fact that each cleavage results in a new 3' hydroxyl and a new 5' phosphate. The increasing presence of either can be measured and enzymatic activity calculated.

In the method according to the present invention, a target polynucleotide may be detected in a series of separate steps or in a homogenous mixture, preferably in a homogenous mixture. The homogenous mixture may comprise all the reagents, including the probe, the 5' exonuclease, one or more buffers, one or more positive controls and one or more negative controls. In some embodiments, all reagents are mixed together at the same time at a temperature compatible to the 5' exonuclease to give a homogeneous assay. In other embodiments, the reagents are added step wise in an order in accordance with the present invention. The reaction may be continued until sufficient probe is cleaved. For example, where the probe is labeled with a 5' quencher and a fluor, the reaction may be carried out until no further increase in fluorescence or when the florescence reaches a threshold value.

The detection limit of the method according to the present invention may be about 1 pmole, preferably about 100 fmole, more preferably about 10 fmole.

For each method according to the present invention, a kit is provided. The kit may comprise all the reagents useful for the method. For example, the kit may comprise all the probes, 5' exonucleases, buffers, positive controls, negative controls and target polynucleotides. Preferably, the kit comprises the probe and the 5' exonuclease.

The term "about" as used herein, when referring to a measurable value such as an amount, a percentage, and the like, is meant to encompass variations of ±20%, ±10%, more preferably ±5%, even more preferably ±1%, and still more preferably ±0.1% from the specified value, as such variations are appropriate.

Example 1. Polymerase Driven NESA

A *Bacillus anthracis* oligonucleotide probe having a sequence of/5IAbFQ/AGGATCTTACGAAACTT/iFluorT/CGG/3AmM/ (10 pmole) (SEQ ID NO: 1) was mixed with a target DNA having a sequence of CCGAAGTTTCGTAAGATCCT (SEQ ID NO: 2) or with water as a control. Reactions were heated at 95° C. for 2 min, cooled to 4° C. for 2 min, where 0.2 μl 5,000 U/ml lambda exonuclease (New England Biolabs) was added. The reaction was warmed to 44° C., and relative fluorescence was determined and plotted after correction for the activity seen with water. Significant relative fluorescence units (RFU) above the nonspecific control (i.e., water) was observed in reactions containing either 10 fmole, 100 fmole or 1 pmole complementary oligonucleotide or one of two *B. anthracis* PCR fragments (S or B) (FIG. 2).

What is claimed:

1. A method for detecting a target polynucleotide in a test sample, wherein the target polynucleotide has a target sequence and is protected against digestion by a 5' exonuclease, wherein the 5' exonuclease is lambda exonuclease, comprising (a) incubating the test sample with a probe having a sequence complementary with the target sequence and lacking a phosphorylated 5' end, wherein the probe has a quencher at its 5' end and a fluor, whereby a hybrid of the probe and the target polynucleotide is formed, wherein the hybrid comprises a hybridization region formed between the target sequence and the probe, wherein the fluor of the probe is quenched by the quencher before forming the hybrid, and wherein the fluor of the probe is quenched by the quencher in the hybrid;

(b) exposing the hybrid to the 5' exonuclease to digest the probe in the hybrid and forming a reaction mixture, whereby a digested probe comprising the fluor is generated, wherein the fluorescence of the fluor of the digested probe is not quenched;

(c) dissociating the target polynucleotide from the digested probe in the reaction mixture;

(d) repeating steps (a)-(c) by adding the probe and the 5' exonuclease to the reaction mixture after step (c), wherein step (b) of step (d) is performed for a first time period until no further increase in the fluorescence in the reaction mixture;

(e) determining a first fluorescence intensity of the fluor in the reaction mixture after step (d);

(f) repeating steps (a)-(d) with a control sample in place of the test sample, wherein step (b) in step (f) is performed for a second time period, wherein the second time period equals to the first time period, wherein the control sample is identical to the test sample except without the target polynucleotide; and (g) determining a second fluorescence intensity of the fluor in the control sample after step (f), wherein the first fluorescence intensity greater than the second fluorescence intensity indicates the presence of the target polynucleotide in the test sample.

2. The method of claim 1, wherein the target polynucleotide is a DNA.

3. The method of claim 1, wherein the target polynucleotide is a RNA.

4. The method of claim 1, wherein the probe has the fluor internally.

5. The method of claim 1, wherein the probe has the fluor at its 3' end.

6. The method of claim 1, wherein the target polynucleotide has one or more nuclease resistant nucleotides upstream of the hybridization region.

7. The method of claim 1, wherein the target polynucleotide has one or more uncleavable linkages upstream of the hybridization region.

8. The method of claim 1, wherein the target polynucleotide is prepared by a polymerase synthesis reaction using a 5' exonuclease protected primer.

9. The method of claim 8, wherein the 5' exonuclease protected primer lacks a 5' phosphate group.

10. The method of claim 8, wherein the 5' exonuclease protected primer contains one or more uncleavable nucleotide linkages.

11. The method of claim 8, wherein the 5' exonuclease protected primer is chemically modified.

12. The method of claim 8, wherein the polymerase synthesis reaction is selected from the group consisting of multiple displacement amplification (MDA), polymerase chain reaction (PCR), rolling circle amplification, nondisplacement amplification and reverse transcription.

13. The method of claim 1, wherein the target DNA polynucleotide is synthesized from one or more short polynucleotides, wherein the one or more short oligonucleotides are resistant to the digestion by the 5' exonuclease.

14. The method of claim 1, further comprising determining the amount of the digested probe.

15. The method of claim 1, wherein the test sample is a homogenous mixture.

16. The method of claim 1, wherein the amount of the target polynucleotide in the test sample is less than 1 pmole.

17. The method of claim 1, wherein the amount of the target polynucleotide in the test sample is less than 10 fmole.

* * * * *